United States Patent
Nicoletti et al.

(10) Patent No.: US 8,563,578 B2
(45) Date of Patent: Oct. 22, 2013

(54) ANTITUMOR PROPERTIES OF NO MODIFIED PROTEASE INHIBITORS

(75) Inventors: Ferdinando Nicoletti, Cannizzaro (IT); Yousef Al-Abed, Locust Valley, NY (US); Gianni Garotta, Lucinges (FR)

(73) Assignee: Onconox APS, Copenhagen (DK)

( * ) Notice: Subject to any disclaimer, the term of this patent is extended or adjusted under 35 U.S.C. 154(b) by 0 days.

(21) Appl. No.: 13/056,696

(22) PCT Filed: Jul. 30, 2009

(86) PCT No.: PCT/EP2009/005526
§ 371 (c)(1),
(2), (4) Date: Apr. 28, 2011

(87) PCT Pub. No.: WO2010/012466
PCT Pub. Date: Feb. 4, 2010

(65) Prior Publication Data
US 2011/0195939 A1    Aug. 11, 2011

Related U.S. Application Data

(60) Provisional application No. 61/085,555, filed on Aug. 1, 2008.

(51) Int. Cl.
*A61K 31/47* (2006.01)
*C07D 217/00* (2006.01)

(52) U.S. Cl.
USPC .......................................... 514/307; 546/146

(58) Field of Classification Search
CPC .............................. C07D 217/00; A61K 31/47
See application file for complete search history.

(56) References Cited

FOREIGN PATENT DOCUMENTS

| WO | 00/61541 | 10/2000 |
|---|---|---|
| WO | 01/12584 | 2/2001 |
| WO | WO 2005/070006 A2 * | 8/2005 |
| WO | WO 2005070006 A2 * | 8/2005 |
| WO | 2006/027711 | 3/2006 |
| WO | WO 2006/027711 A3 * | 3/2006 |
| WO | WO 2006027711 A2 * | 3/2006 |

OTHER PUBLICATIONS

Fiorucci, S. et al. NSAIDs, coxibs, CINOD and H2S-releasing NSAIDs: What lies beyond the horizon. Digestive and Liver Disease. 2007, vol. 39, p. 1047, left top paragraph.*

Maksimovic-Ivanic et al., "The antitumor properties of a nontoxic, nitric oxide-modified version of saquinavir are independent of Akt" Molecular Cancer Therapeutics, vol. 8, No. 5, May 2009, pp. 1169-1178.

Chai et al., "Effects of 5 HIV protease inhibitors on vasomotor function and superoxide anion prodcution in procine coronary arteries" Journal of Acquired Immune Deficiency Syndromes, 1999, vol. 40, No. 1, pp. 12-19.

Sehajpal et al., "Reversible S-nitrosation and inhibition of HIV-1 protease" Biochemistry, vol. 38, No. 40, Oct. 5, 1999, pp. 13407-13413.

* cited by examiner

*Primary Examiner* — Rita Desai
*Assistant Examiner* — Ben S Michelson
(74) *Attorney, Agent, or Firm* — Lucas & Mercanti, LLP

(57) ABSTRACT

HIV-protease inhibitors, particularly saquinavir, showed strong anticancer activity but numerous side effects limited its application. In order to overcome its toxicity original compounds were modified by covalent attachment of NO. The efficacy of parental and NO-modified drug was compared in vitro and in vivo. Anticancer activities of NO-modified saquinavir (Saq-NO) was monitored in vitro using assay for cell viability, proliferation, necrotic, autophagic and apoptotic cell death, differentiation, expression of intracellular molecules such as cyclin D3, p53 and Akt. Antitumor properties and toxicity of the compound was estimated in vivo. Saq-NO abrogated the viability of large spectrum of human and rodent tumor cell lines with IC50 significantly lower than parental drug and expressed strong antimelanoma action in vivo. In contrast to saquinavir, there was no detectable toxicity against primary cells in vitro and in vivo. Saq-NO permanently diminished cell proliferation by induction of cell cycle block accompanied with minor presence of tumor cell death. Repressed proliferation was coordinated with strong activation of p53 and differentiation of C6 and B16 cells into oligodendrocytes or "Schwan" like cells, respectively. Oppositely to general characteristic of saquinavir to inhibit Akt signalling, Saq-NO treatment resulted in transient and intensive upregulation of Akt. This antagonism between parental and modified compound could be the crucial for switch of saquinavir from toxic to completely untoxic drug.

5 Claims, 7 Drawing Sheets

A

B

C

ANTITUMOR PROPERTIES OF NO MODIFIED PROTEASE INHIBITORS

Figure 1:
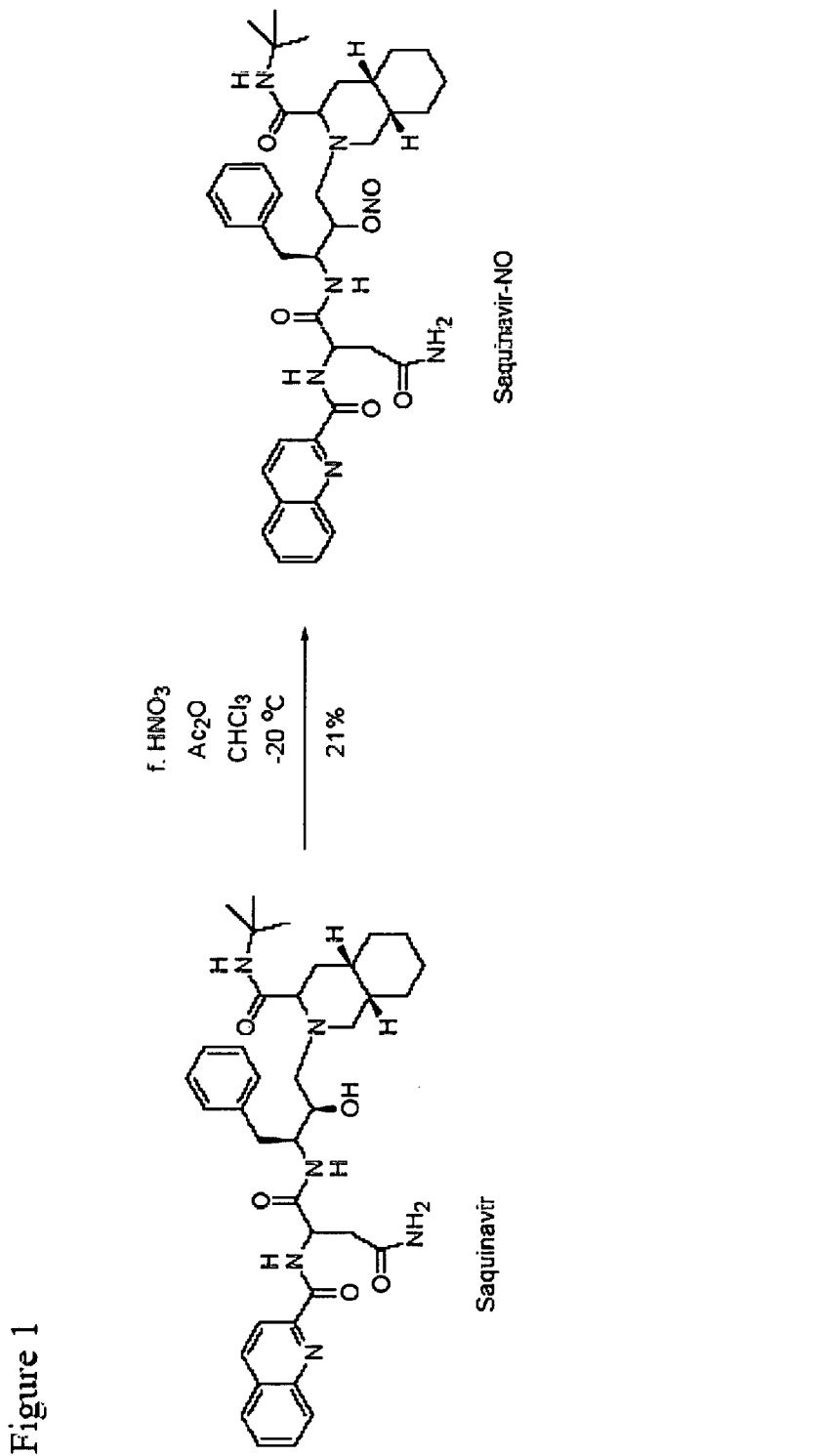

This application is a U.S. national stage of PCT/EP2009/005526 filed on Jul. 30, 2009 which claims priority to and the benefit of U.S. Provisional Application No. 61/085,555 filed on Aug. 1, 2008, the contents of which are incorporated herein by reference.

The present invention concerns the nitric ester of HIV protease inhibitors, particularly of Saquinavir and their use thereof in human therapy.

BACKGROUND OF THE INVENTION

HIV protease inhibitors (HIV-PIs) are antiretroviral agents approved for human use since 1993. HIV-PIs are designed to bind to the catalytic site of HIV protease selectively and thus block the replication and production of infective viral particles (Decks et al 1997). It was shown that these drugs affected several important cellular processes such as angiogenesis, inflammation, processing and presentations of antigens, cell survival and tissue remodelling (Sgadari et al. 2003, Andre et al. 1998, Gruber et al. 2001, Delmonte et al. 2007). Recent evidence indicated strong anticancer capacity of HIV-PIs both in vitro and in vivo. Inhibition of growth of different tumor cells was accompanied with the induction of apoptotic cell death (Chow et al. 2006, Pajonk et al. 2002, Ikezoe et al. 2004, Ikezoe et al. 2000, Gills et al. 2007). Despite the fact that the mechanisms of action of these drugs are not strictly defined, their potential targets are: AKT, extracellular signal-regulated kinase, nuclear factor-kB, signal transducers and activators of transcription 3, matrix metalloproteinase, basic fibroblast growth factor (FGF) and vascular endothelial growth factor (VEGF) (Pajonk et al. 2002, Ikezoe et al. 2004, Sgadari et al. 2002, Ikezoe et al. 2004, Gupta et al. 2005, Cuneo et al. 2007). Moreover, it was shown that these drugs sensitize tumor cells to radiation, enhance the anticancer effects of other cytostatic drugs and also inhibit growth and invasion of angiogenic tumor cells in nude mice (Ikezoe et al. 2004, Sgadari et al. 2002, Gupta et al. 2005).

Unfortunately, the application of these drugs was followed with many unpredicted and adverse effects such as hyper- or hypolipidaemia, cardiovascular diseases, diabetes, body fat redistribution, osteopenia and osteoporosis (Flexner, 1998). Addition of NO moiety is one of the current approaches employed in order to reduce toxicity and enhance drug efficacy. This type of chemical modification was applied on numerous non-steroidal anti-inflammatory drugs.

DESCRIPTION OF THE INVENTION

It has now been found that HIV protease inhibitors, particularly Saquinavir, may be advantageously modified by covalent attachment of NO.

The invention accordingly provides nitric esters of HIV protease inhibitors.

The $NO_2$ moiety is introduced on the hydroxy group present on the known protease inhibitors by conventional methods, i.e., by reaction with concentrated nitric acid in acetic anhydride/halogenated hydrocarbon at temperatures lower than 0° C., preferably lower than −10° C.

Examples of proteases inhibitors which, in addition to Saquinavir, can be advantageously esterified with nitric acid, include Ritonavir, Nelfinavir, Indinavir, Darunavir, Lopinavir, Amprevanir, Atazanavir.

The nitric ester of Saquinavir is particularly preferred, having formula I

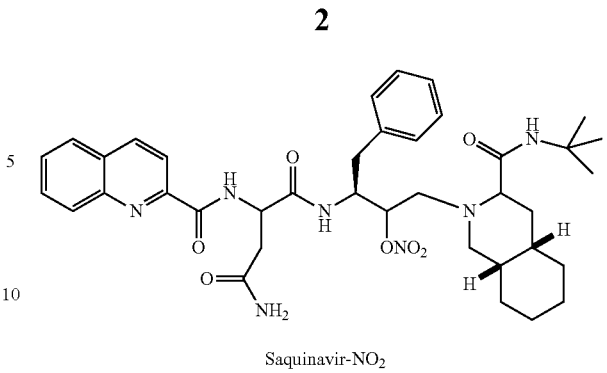

Saquinavir-$NO_2$ as well as its non-toxic salts, solvates or crystalline/polymorphic forms.

The compound of formula I, hereinafter designated as $NO_2$-Saquinavir, was found to be more effective and less toxic than the patent compound saquinavir, as it will be shown in the experimental part reported below.

The synthetic scheme of compound I is reported in FIG. 1.

The invention also provides pharmaceutical compositions comprising the compound of formula I or other nitric ester of HIV protease inhibitors in admixture with suitable carrier/excipients. The compositions of the invention may be administered by any known route, particularly by the oral, parenteral, topical, transdermal, rectal route.

The dosage will be easily determined by any skilled practitioner according to the toxicological, pharmacokinetics and pharmacodynamic properties as well as according to the patients' conditions (severity of the disease and degree of advancement), weight, age and sex. The dosages will be generally similar to that already known in clinical practice for the parent compound saquinavir or for the corresponding parent protease inhibitors.

Said compositions are useful for the treatment of tumors and of HIV infections.

The invention accordingly provides also a method of treatment of patients affected by tumors and/or HIV infections comprising the administration to said patients of an effective amount of the compound of claim 1.

The following examples describe the invention in more detail.

EXAMPLE 1

Saquinavir NO Saquinavir $NO_2$ Synthesis

Saquinavir (3 g, 4.48 mmol) in $CHCl_3$ (18 mL) was added to a stirring mixture of fuming nitric acid (≥90% $HNO_3$, 1 mL, 23.6 mmol) and $Ac_2O$ (3.5 mL, 37.1 mmol) at −10° C. and then slowly warmed up to room temperature in two hours under nitrogen. The reaction mixture was quenched with ice cold water and extracted with $CH_2Cl_2$. The extracts were washed with ice cold saturated $NaHCO_3$ and water, dried with $MgSO_4$ and filtered. The solvent was evaporated under pressure and the crude product was purified by FCC eluting with 3:2 to 3:3 Hex:Acetone. The product obtained was recrystallized from EtOAc/Hex to give the Saquinavir-$ONO_2$ (1.7 g, 53%) as a white solid and the purity was analyzed by HPLC and MS. MS m/z 716.33 (M+H$^+$).

HPLC: Column type: Phenomenex primesphere 5 C18 MC 110A 250×4.6 mm.

Detected wavelength: 275 nm (maximum absorbance wavelength).

Flow rate: 1 mL/min with a linear gradient from Water (0.1% AcOH):

MeOH [90:10] to Water (0.1% AcOH): MeOH [10:90] in 30 min

EXAMPLE 2

Biological Characterisation

Materials and Methods
Reagents and Cells

Acridin orange (AO) was obtained from Labo-Moderna (Paris, France). Carboxyfluorescein diacetate succinimidyl ester (CFSE) was from Molecular Probes (Eugene, USA). Inhibitor Akt VI was obtained from Calbiochem (Germany). All other chemicals were purchased from Sigma (St. Louis, USA) unless specified otherwise. Saquinavir (Saq, MW 670 g/l) and Saquinavir-$NO_2$ (Saq-$NO_2$, MW 715 g/l) were stored at −20° C., at concentration of 5 mg/ml in 25% of dimethylsulfoxide (DMSO) in RPMI 1640-5% FCS, and they were diluted in culture medium immediately before use. Control cell cultures were treated with an adequate volume of DMSO.

Rat glioma C6 and human glioblastoma U251 cell lines were a kind gift from Dr. Pedro Tranque (Universidad de Castilla-La Mancha, Albacete, Spain), murine melanoma B 16, and human adenocarcinoma HeLa, were a kind gift from Dr. Sinisa Radulovic (Institute for Oncology and Radiology of Serbia, Belgrade, Serbia) while mouse fibrosarcoma L929 was obtained from the European Collection of Animal Cell Cultures (Salisbury, UK). Human breast HCC1419 and prostate PC-3 cells were purchased from LGC Promochem srl (Venezia, Italy). Primary mouse fibroblasts and rat astrocytes were prepared as described (Mijatovic et al. 2004). Cells were grown in HEPES-buffered RPMI 1640 medium supplemented with 5% FCS, 2 mM glutamine, 0.01% sodium pyruvate, $5 \times 10^{-5}$ M 2-mercaptoethanol, and antibiotics (culture medium) at 37° C. in a humidified atmosphere with 5% $CO_2$. After the conventional trypsinization procedure cells were seeded at $1 \times 10^4$/well in 96-well, $2 \times 10^5$/well in 6-well plate or $3 \times 10^4$/well in 4-well chamber slide, cultivated overnight, and then exposed to drug. Inbred C57BL/6 2-3 months old mice were obtained from our facility at the Institute for Biological Research "Sinisa Stankovic" and were kept under standard laboratory conditions (non specific pathogen free) with free access to food and water. The handling of animals and the study protocol were in accordance with international guidelines and approved by the local Institutional Animal Care and Use Committee.

Cell Viability Determination by MTT, Crystal Violet and LDH Release Assay

Reduction of 3-4,5-dimethylthiazol-2-yl)-2,5-diphenyltetrazolium bromide (MTT) to formazan depends on mitochondrial activity of cultured cells, absorption of crystal violet dye correlates with the number of adherent, live cells, while the release of cytosolic lactate dehydrogenase (LDH) indicates the disruption of membrane integrity caracteristic for necrotic cells. The cells were seeded in flat-bottom 96-well plates in a final volume of 200 µl of culture medium containing different agents, and the assays were performed after 24 h incubation exactly as previously described (Mijatovic et al. 2004, Decker et al., 1998). Mitohondrial-dependent production of formazan and intensity of absorbed crystal violet by adherent cells were assessed by an automated microplate reader at 570 nm, while the pyruvate-mediated conversion of 2,4-dinitrophenylhydrazine into visible hydrazone precipitate in LDH assay was measured at 492 nm. The % of cytotoxicity as indicated by LDH release was calculated as: $(E-C)/(T-C) \times 100$, where E is the experimental absorbance of cell cultures, C is the control absorbance of cell-free culture medium, and T is the absorbance corresponding to the maximal (100%) LDH release of Triton-lysed cells.

Determination of Cell Proliferation

Rate of cell proliferation was verified by flow cytometric analysis of cells labelled with CFSE (Kang et al. 2005). CFSE dye is stable in cytoplasm more than 15 generations and the intensity of fluorescence decline after each division. Briefly, detached cells were stained with 1.5 µM CFSE for the 15 min at 37° C., washed 2 times, seeded in 6-well plates at $2 \times 10^5$ cells/well and then exposed to drugs. After 24 and 48 h of cultivation cells were trypsinized and washed 2 times. Finally, the cells were resuspended in PBS and analyzed by flow cytometry. Green fluorescence emission was measured with a FACSCalibur (BD, Heidelberg, Germany) and analyzed using CellQuest software.

Determination of Apoptotic and Autophagic Cell Death

Apoptotic cell death was assessed by flow cytometry analysis of DNA fragmentation in cells stained with DNA-binding dye propidium iodide (PI). Following a 24 h incubation in 6-well plate, cells ($2 \times 10^5$/well) were detached with trypsin, washed and fixed in 70% ethanol at 4° C. for 30 min. After washing in PBS, cells were resuspended in PBS containing 1 mg/ml RNase and propidium iodide (40 µg/ml) and kept at 37° C. in the dark for 30 min. Red fluorescence was analyzed with FACSCalibur flow cytometer (BD, Heidelberg, Germany) and distribution of cells among cell cycle phases was determined with Cell Quest Pro software (BD). Hypodiploid cells in sub-$G_0/G_1$ compartment were considered apoptotic.

Vital dye acridin orange (AO) was used for detection of autophagy. The intensity of red fluorescence correlates with acidity and volume of present autophagic organelles (Kanzawa et al. 2004). Assay was performed as follows: the cells were cultured in 6-well plate ($2 \times 10^5$/well) 24 h in the presence of the drug, detached with trypsin and stained with 1 µg/ml AO in RPMI without phenol red for 15 min at RT. After the end of incubation period cells were washed and resuspended in PBS. Green and red fluorescence emission was measured with a FACSCalibur and analyzed using CellQuest software.

Measurement of NO Release and Nitrite Accumulation

Nitrite accumulation as indirect measure of NO release was measured by Griess reaction as described previously (Mijatovic et al. 2004). For intracellular NO detection cells were stained for 1 h at 37° C. with 2 µM of NO indicator DAF-FM diacetate (Molecular Probes) in phenol red-free RPMI 1640. The cells were then washed and incubated for additional 15 min at 37° C. in fresh RPMI 1640 before drug treatment. After 2 h cells were trypsinized, washed and finally resuspended in PBS and analyzed by FACSCalibur using Cell Quest software.

Cell-based ELISA

A slightly modified method for cell-based ELISA (cELISA) by Versteeg (Versteed et al., 2000) was used to measure the expression of galactocerebroside, glial fibrilar acidic protein (GFAP), myelin basic protein (MBP), cyclin D3, p53 and p-AKT. Briefly, at the end of cultivation period cells were fixed in 4% paraformaldehyde, endogenous peroxydase was quenched with 1% $H_2O_2$ in PBS containing 0.1% Triton X-100 (PBST), and unspecific binding of antibodies blocked with PBST solution containing 10% FCS. Primary mouse monoclonal antibodies specific for rat/mouse p-Akt (1:200; Santa Cruz Biotechnology, Santa Cruz, Calif.), GFAP (1:200, BioYeda, Israel.), galactocerebroside (1:100; Boehringer Mannheim, Mannheim, Germany), MBP (1:100, Boehringer Mannheim, Mannheim, Germany), cyclin D3

(1:750, Santa Cruz Biotechnology, Santa Cruz, Calif.) and p53 (1:250, Santa Cruz Biotechnology, Santa Cruz, Calif.) were applied in PBST supplemented with 2% bovine serum albumin (PBSTB), followed by secondary peroxidase-conjugated goat anti-mouse IgG (1:2500 in PBSTB; GE Healthcare UK) for anti-GFAP and galactocerebroside or anti-rabbit IgG (1:2500, Healthcare UK) for anti-p-Akt, anti-cyclin D3 and anti-p53. All incubations were performed at 37° C. for 1 h. The absorbance at 450 nm was measured in an automated microplate reader 15 min after incubation with peroxydase substrate TMB and subsequently to addition of 0.1 M HCl. To facilitate comparison between treatments, the obtained absorbances were corrected for the cell number that was determined by crystal violet staining, as described in the original protocol. The results are presented as relative expression in comparison with the control value.

Tyrosinase Activity Assay and Melanin Determination

Tyrosinase activity was determined by measuring the rate of oxidation of L-DOPA[34]. Briefly, sub-confluent cultures in 6-well plate were lysed in 100 µl phosphate buffer pH 6.8-1% Triton X-100 and than centrifuged at 10000 rpm for 5 min. 40 µl of each extract was mixed with 100 µl of L-DOPA substrate solution (2 mg/ml). Enzymatic reaction was carried out at 37° C. and the absorbance at 570 nm was read every 10 min for at least 1 h. The final activity was corrected by the total amount of protein estimated by Bradford assay. For melanin determination cells were incubated in 6 well plate for 24 h, trypsinized, counted and than lysed in 100 µl of 1M NaOH. 400 µl of distilled water was added and samples were incubated at 60° C. for 1 h. Thereafter, absorbance of dissolved dye was measured at 492 nm.

Immunocytochemical Detection

The detection of expression of cyclin D3 and p53 expression was performed by the immunocytochemical procedure as previously described (Mijatovic et al, 2005). The cells were cultivated in glass chamber-slides ($3 \times 10^4$ cells/well) and cyclin D3 and p53 expression were detected with specific antibodies against cyclin D3 (1:1000, Santa Cruz Biotechnology, Santa Cruz, Calif.) and p53 (1:500, Santa Cruz Biotechnology, Santa Cruz, Calif.). Recognition of primary antibodies was performed with rabbit extravidin-peroxidase staining kit according to the manufacturer's instructions (Sigma) using diaminobenzidine (R&D Systems, Minneapolis, Minn.) as a substrate. The cells were counterstained with Mayer's hematoxylin and slides were mounted with glycergel mounting medium (Dako, Glostrup, Denmark).

Western Blot Analysis

Cells ($1 \times 10^6$) were seeded in flasks (25 cm$^3$), incubated in 0.5% FCS RPMI over night and subsequently treated with drugs for 30, 60 and 120 min. Whole-cell lysates were prepared in a solution containing 62.5 mM Tris-HCl (pH 6.8 at 25° C.), 2% w/v SDS, 10% glycerol, 50 mM DTT, 0.01% w/v bromophenol blue, and were subjected to electrophoresis on a 12% SDS-polyacrylamide gel. The samples were electro-transferred to polyvinylidene difluoride membranes at 5 mA/cm$^2$, using semi-dry blotting system (Fastblot B43, Biorad, Goettingen, Germany). The blots were blocked with 5% w/v nonfat dry milk in PBS 0.1% Tween-20 and probed with specific antibodies to p53, CD3, Akt, phosphorilated-Akt and actin (all were diluted 1:1000; Akt, p-Akt were from Cell Signalling Technology, Boston, Mass.; CD3, p53 and actin were from Santa Cruz Biotechnology, Santa Cruz, Calif.), followed by incubation with secondary antibody (ECL donkey anti-rabbit HRP linked, GE Healthcare, Buckinghamshire, UK). Detection was performed by the chemiluminescence (ECL, GE Healthcare).

Induction of Melanoma in C57BL/6 Mice and Drugs Treatment

In order to induce primary tumor $2 \times 10^5$ B16 melanoma cells were injected subcutaneously (s.c) in the dorsal right lumbosacral region of syngeneic C57BL/6 mice. Tumor growth was observed daily, and the drug treatment started from day 10 after implantation. Fresh solutions of Saq and Saq-NO$_2$ was injected intraperitoneally (i.p.) at a dose of 10 mg/kg body weight for 15 consecutive days. Mice were sacrificed on day 30, tumor growth was determined by three-dimensional measurements of individual tumors from each mouse. Tumor volume was calculated as: $[0.52 \times a \times b^2]$, where a is the longest and b is the shortest diameter as described previously (Maksimovic-Ivanic et al. 2008).

Acute Toxicity

To define the acute toxicity of Sag and Sag NO$_2$, the test compound was administered i.p. to CD1 mice at the single doses of 250, 500, 1000 and 1500 mg/Kg. Control groups were treated i.p. with vehicle (pure DMSO; 100 µl/mouse). Each group consisted of 10 mice. Mortality was evaluated every hour for the first 4 hours and then every 10 hours until 14 days after dosing.

Statistical Analysis

The significance of the differences between various treatments was analysed by ANOVA followed by Student-Newman-Keuls test for multiple comparisons. A p value less than 0.05 was considered to be significant.

Results

Sag-NO$_2$ Strongly Decreased the Viability of Tumor but not Primary Cells

The effect of Saq and Saq-NO$_2$ was evaluated on the viability of distinct transformed human (HeLa cervix adenocarcinoma, BT20 and HCC 1419 breast carcinoma, PC-3 prostate carcinoma) and rodent (C6 rat astrocytoma and B16 mouse melanoma) cell lines, as well as the primary non-transformed cells (rat primary astrocytes and mouse fibroblasts). As evaluated by crystal violet assay (FIG. 2A, 2B) and mitochondrial respiration (not shown), both compounds exhibit strong anti-tumor potential. NO-modified compound was more efficient, with IC50 value two to four fold lower than the parent drug. Interestingly, additional increase of Saq-NO concentrations did not further decrease further viability. Moreover, Saq-NO did not affect the viability of non-transformed primary astrocytes and fibroblasts, while IC50 dose of Sag was highly toxic (FIG. 2C). Thus, it was evident that attachment of NO to the parent compound strongly enhanced its tumoricidal potential and almost totally abrogated its toxicity against primary cells. To delineate the cytotoxic mechanisms of the two different Sag preparations we used C6 and B16 rodent cell lines as representative.

Saq-NO$_2$ release negligible amount of NO. Observed enhancement of Saq tumoricidal action after its chemical modification could be the consequence of quantity and kinetics of NO release. In order to assess the magnitude of NO release by the drug, the intracellular accumulation of NO and its liberation in cell culture supernatants after 24 h of tumor cell incubation were measured in the presence of Saq-NO$_2$. Surprisingly, unlike other NO modified drugs, Saq-NO$_2$ treatment induced minor intracellular release of NO in both B16 and C6 cells (FIG. 3A). Concordantly, negligible NO release was observed in cell culture supernatants (FIG. 3B). These data suggest that minor amount of NO liberated from the drug could not be directly responsible for drug induced toxicity against malignant cells and that such structural modification of parental drug gave qualitatively new pharmacological profile, quite distinct from other NO donating compounds.

Antitumor activity of Saq-NO$_2$ was mainly based on cytostatic activity. In the following experiments, the ability of Saq and Saq-NO$_2$ to induce different types of cell death was compared. The presence of necrosis by LDH release assay was first analyzed. The test is based to the feature of necrotic cell to release LDH into cell supernatant due to cell membrane damage. As seen in FIG. 4A, treatment of C6 and B16 cells with Saq induced LDH release in both cell lines in a dose-dependent way, suggesting the importance of necrotic cell death as primary or secondary mechanism of drug action. However, significant percentage of C6 cytotoxicity was detected only upon the highest dose treatment with Saq-NO$_2$ indicating that necrosis is not responsible for observed antiglioma activity of new compound. On the other hand, in melanoma cells dose-dependent LDH release was detected upon all tested doses of Saq-NO treatment (FIG. 4A). Moreover, Saq-NO$_2$ induced significant cytoxicity even at lowest dose tested, indicating higher B16 sensitivity to Saq-NO$_2$ than to Saq. Additionally, significant release of LDH could not be detected before 18 h of exposure to the drug (2.3% in controls vs 6.2% in 18.8 μM Saq-NO treated cultures), indicating that necrosis is rather the consequence than the primary mechanism of drug action. For further investigation the dose of 18.8 μM of Sag-NO that reduced cell viability for approximately 50% in C6 and 70% in B16 was selected and compared with the same dose of Sag. In view of the fact that B16 and C6 cells are known as autophagy prone cells, the contribution of authophagy in anti-tumor effects of both drugs was evaluated. Neither Sag-NO nor Sag increased the amount of acidic vesicles in the cytoplasm of both cell lines pointed out the absence of autophagia either as dying or salvaging process (FIG. 4B).

The influence of the drugs on cell cycle distribution was then assessed. Cells treated with Saq did not show considerably different distribution from control, untreated cells (FIG. 4C). In C6 cell cultures Saq-NO$_2$ slightly increased the percentage of cells in subG compartment and induced particularly marked arrest in G$_0$/G$_1$ (FIG. 4C, left panel). In parallel, the same treatment of B16 cells resulted in statistically significant apoptosis and accumulation of cells in G$_2$/M phase of cell cycle (FIG. 4C, right panel). Dominant cell cycle block followed with small presence of apoptosis, absence of autophagic and necrotic cell death in glioma cells raised the possibility that inhibition of proliferation rather than induction of cell death is mechanism responsible for antitumor properties of Saq-NO$_2$. The dominance of cytostatic activity of the drug was further confirmed by CFSE staining While about 90% of control cells are divided after 48 h, upon the Saq-NO$_2$ treatment less than 10% of cells are able to proliferate (FIG. 4D, left panel). B16 cells, which survived the treatment with Saq-NO$_2$ showed decreased dividing potential as C6 cells suggesting the priority of this mechanism in the compounds action. Moreover, while Saq withdrawal mainly restored the viability of cells after 24h, removal of Saq-NO$_2$ in the same conditions resulted in very mild recovering, thus suggesting that loss of proliferative capacity was permanent (FIG. 4D, right panel). In summary, these results strongly indicated the superior cytostatic capacity of Saq-NO$_2$.

Sag-NO$_2$ induced differentiation of neuroectodermal C6 and B16 cells. Inhibition of cellular proliferation as a result of drug treatment was accompanied with morphological transformation of both tumor cell lines tested (FIG. 5A). To further explore if those morphological features correlated with phenotypic changes we analyzed the expression of differentiation markers in C6 and B16 cell cultures. In view of the fact that the expression of oligodendrocytic marker, galactocerebroside, was strongly up regulated, whereas the expression of GFAP was decreased or unchanged (FIG. 5B, left panel), it seemed that C6 cells after the treatment with Saq and particularly Saq-NO$_2$ adopted the phenotype of oligodendrocytes rather than astrocytes. On the other hand, increased melanin content and activity of tyrosinase of B16 cells only after the treatment with Saq (FIG. 5B, right panel), and observed morphological transformation (FIG. 5A, right panel) indicated that cells acquired the melanocytic phenotype. In contrast, beside evident morphological transformation triggered by Saq-NO$_2$, B16 cells showed slight but significant decrease in tyrosinase activity and unchanged melanin quantity. In parallel, those cells showed mild elevation of MBP expression (FIG. 5B, right panel), indicating that B16 cells adopted the phenotype of so called "Schwann-like cells". This process was described in literature as "transdifferentiation" (Reed JA, 1999) and presented the final stage before involution of melanocytes.

According to relevance of cyclin D3 and tumor suppressor protein—p53 expression in oligodendrocytic development, their involvement in differentiation process triggered by tested compounds was next investigate in C6 and B16 cells. After 24 h of incubation in the presence of Saq and Saq-NO$_2$, cyclin D3 and p53 protein expression was determined by cELISA (FIG. 5C, upper panels) and imunocytochemistry (FIG. 5C, lower panels) Western blot analysis confirmed the same phenomenon only 4h after exposure to the drug (FIG. 5C, middle panels). While treatment of cells with Saq resulted in upregulated activity of cyclin D3 and p53, Saq-NO$_2$ affected p53 expression in much higher extent than Saq, whereas the expression of cyclin D3 in both cell lines was not considerably changed (FIG. 5C). Taken together, covalent NO$_2$ attachment to Saq generated significant differences of drug activity at the intracellular level.

Saq and Saq-NO$_2$ oppositely regulate the AKT signalling pathway. It is well documented that PI-3K-Akt signalling pathway is one of the most important intracellular targets of Saq and other HIV- PIs, that could be relevant for their tumoricidal properties but also responsible for the observed high toxicity of this family of drugs. Having in mind previous data about conserved antitumor properties of the modified HIV protease inhibitor-Saq-NO$_2$ and absence of its toxicity against normal cells, we next investigated possible influence of the drug on the Akt-mediated signalling pathway. Obtained results clearly indicated that Saq abrogated p-Akt expression even in this quite ineffective dose while, entirely opposite to it, Saq-NO$_2$ induced considerable transient phosphorylation of AKT. Both drugs, modified and original compound, demonstrated similar mode of action in B16 and C6 cells, and results obtained by cELISA and Western blot analysis were presented on B16 cells as representative (FIG. 6A, 6B). Moreover, treatment of cells with specific inhibitor of up-stream PI-3 kinase, 3-MA, or inhibitor of Akt, AKT VI, resulted in further decrease of tumor cell viability (FIG. 6B). The results clearly indicated that conserved and even potentiated antitumor activity of NO$_2$ modified compound was not mediated by inhibition nor upregulation of Akt activity. Moreover, potentiation of Akt activity presented a protective signal and could be a major candidate for lack of the toxicity in primary cells exposed to this NO$_2$ modified compound.

Figure 7:
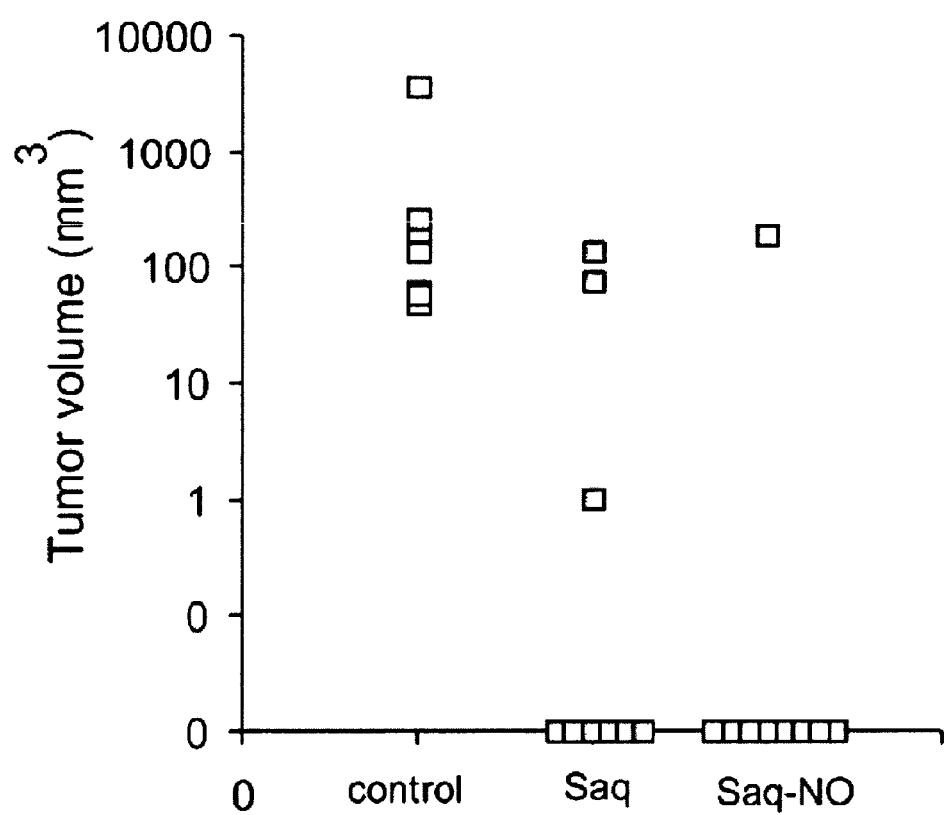

Saq and Saq-NO$_2$ reduced B16 melanoma growth in syngeneic C57BL/6 mice. In order to investigate and compare the in vivo antitumor properties of parental and newly generated compound, B16 tumor cells were inoculated s.c. into syngeneic C57BL/6 mice, and then treated i.p. with either Saq or Saq-NO$_2$. Drug treatment started 10 days after tumor induction and lasted for 15 consecutive days. As seen in FIG. 7, at autopsy (day 30 post tumor challenge) all control animals developed solid tumors. In group treated with Saq, 3/9 animals developed tumors, but with significantly reduced volume. Finally, only one tumor was observed in Saq-NO$_2$ treated group. In parallel, animals receiving Saq showed remarkable loss of body weight (10% from initial body weight) and 4 animals without tumors showed strong inflammation of peritoneum. On the other hand, no any visible signs of toxicity were seen upon the Saq-NO$_2$ treatment; moreover animals raised their body weight (13% of initial body weight).

In vivo Toxicity of Saq and Saq-NO$_2$

While no mortality was observed in all the tested doses of Saq-NO$_2$, Saq was capable of induce 100% of lethality at the dose of 1500 from 18 to 144 hours (mean±SD =65±58), 30% at the dose of 1000 mg/Kg and 20% at the dose of 500 mg/Kg within 24 hours after administration.

Discussion

It was recently shown that HIV-PIs in addition to its primary ability to inhibit HIV protease possessed strong antitumor features. HIV-PIs are able to inhibit the growth of numerous type of tumor cell lines such as multiple myeloma, SW872 liposarcoma, T24 bladder carcinoma, A549 lung carcinoma, U373 glioblastoma, Jurkat leukemia cells, DU-145 and PC-3 prostate cancer cells, NB4 and HL-60 human myelocytic leukemia cells and Kaposi's sarcoma (Chow et al. 2006, Pajonk et al. 2002, Ikezoe et al. 2004, Ikezoe et al. 2000, Gills et al. 2007). Moreover, those drugs were capable to decrease incidence and promote regression of Kaposi's sarcoma, and to amplify the therapeutic efficacy of radio- and chemotherapy of the head, neck, bladder and prostate cancers (Pajonk et al. 2002, Ikezoe et al. 2004, Sgadari et al. 2002, Ikezoe et al. 2004, Gupta et al. 2005, Cuneo et al. 2007). However, long-lasting administration of this type of drugs causes unpredicted adverse effects like hyperbilirubinaemia, hyperlipidaemia or hypolipidaemia, insulin resistance and diabetes etc. (Sgadari et al. 2003).

The compound of the invention, Saq-NO$_2$ resulted in potentiation of antitumor properties and abrogation of toxicity against normal tissue. In more details, different mode of newly synthesized drug action was linked with higher potency in suppression of growth of several rodent and human tumor cell lines. Furthermore, the toxicity towards primary cells was almost completely overcome. While it is considered that NO release from other NO donating compounds is directly or indirectly responsible for their cytotoxicity (Rigas et al. 2004), Saq-NO$_2$ liberates just minimal quantity of NO which is not strong enough to be cytotoxic but could actually be the modulator of numerous intracellular events. The limitation of tumor cell expansion induced by Saq is mainly a consequence of induction of apoptosis (Ikezoe T at al. 2004). While this type of programmed cell death is crucial for diminished viability of C6 and B16 cells exposed to higher doses of Saq, the contribution of tumor cell death (accidental or programmed) upon cultivation with modified compound is minor. Concordantly with obvious decrease of tumor cell viability, observed cell cycle arrest and CFSE staining confirmed that inhibition of proliferation is crucial for anticancer activity of Saq-NO$_2$. In agreement with this, cells were still incapable to divide even after drug withdrawal, suggesting that loss of proliferative properties was permanent. In parallel, the drug promoted significant morphological alteration of C6 and B16 cells indicating phenotypic transformation of malignant precursors. Capacity of C6 and B16 cells to differentiate is well documented. Depending of stimulus, C6 cells possesses bidirectional differentiation capacity. Thus, it was shown that upon exposure to antraquinone Aloe emodin, as well as to *Datura stramonium* agglutinin and staurosporine—potent PKC inhibitor—C6 cells underwent differentiation towards astocytic linage, while other agents such as saicosaponins A and D isolated from Bupleurum Radix promoted maturation into oligodendrocytes (Mijatovic et al. 2005, Tsai et al. 2004, Sasaki et al. 2002, Kronfeld I et al. 1995). B16 cells, originated from the same embryonal precursors as C6, triggered by α-melanocyte stimulating hormone, ultraviolet A and B radiation, as well as pharmacological agents such forskolin, cholera toxin, isobutylmethylxantine, retinoic acid, and mannosylerythritol lipid, obtained the characteristics of primary melanocytes (Busca et al. 1996, Busca et al. 1998, Valverde et al. 1993, Bennet et al. 1994, Ohguchi et al. 2004, Gruber et al. 1992, Zhau et al. 1999). According to this, determination of expression of relevant differentiation markers upon the treatment with both, parental or NO$_2$-modified compound revealed that C6 cells entered in the process of differentiation into oligodendrocytes. It was previously described that some of HIV-PIs induce the preadipocyte and human myelocytic leukemia cells differentiation (Ikezoe et al 2000, Chow et al 2006, Nguyen et al. 2000). On the other hand, while Saq induced the differentiation of B16 cells toward melanocytes, Saq-NO$_2$ showed the opposite effects on melanin synthesis and tyrosinase activity. It was found that some circumstances drive B16 into process known as "trans-differentiation" with resulting Schwan like phenotype (Slutsky et al. 2003). It was considered that this cell profile is actually the end point in natural melanocytes involution route (Reed JA et al. 1999). Downregulated melanocytic markers after Saq-NO$_2$ exposure were followed with elevated expression of MBP suggesting that this treatment pushed the B16 cells directly into the end stage of melanocytes life spine.

Tokomonto et al (Yasuhito M. Tokumoto, Be'atrice Durand, 1 and Martin C. Raff, 1999) have previously established the connection between cyclin D3 expression and oligodendrocytic development promoted by PDGF withdrawal or thyroid hormone treatment. Upregulation of cyclin D3, most widely expressed cyclin D family member in mammals (Bartkova et al., 1998) was observed in some myoblast cell lines (Jahn et al., 1994; Kiess et al., 1995; Rao and Kohtz, 1995) and human promyelocytic leukaemia line HL 60 (Bartkova et al., 1998) in the process of differentiation. Furthermore, thyroid hormone induced oligodendrocytic maturation of multipotential stem cells (Johe et al., 1996 Ahlgren et al., 1997; Barres et al., 1994; Ibarolla et al., 1996) was tightly related to cyclin D3 upregulation as well as increased level of p53 expression. The former is described in literature as principal molecule which leads precursor cells to oligodendrocytic linage. Differentiation of C6 and B16 cells triggered by the Saq, correlated with elevated accumulation of cyclin D3 which is probably the consequence of its 26S protesome inhibiting properties (Pajonk, 2002). On the other hand, the level of cyclins D3 was not affected by Saq-NO$_2$. Discrepancy in regulation of p53 and cyclin D3 by the two drugs, but with similar outcome of C6 tumor cell maturation opens the question of cyclin D3 priority in this process. In addition, significantly higher quantity of p53 protein after Saq-NO$_2$ exposure in both cell lines tested in comparison to cultures treated with parental compound is compatible with data of pivotal role of p53 protein in neuronal tissue cell differentiation (Billon et al. 2004). According to this, upregulated activity of p53 could be responsible for the observed Saq and specially Saq-NO$_2$ promoted differentiation of C6 and B16 cells and consequent development of nonmalignant and non-dividing cells with recognizable phenotype—oligodendrocytes and Shwann-like cell.

It was well documented that HIV-PIs activity interfered with PI-3K-Akt signalling pathway. For example, nelfinavir, amprenavir and saquinavir were capable to inhibit Akt activity in numerous cell lines, but mechanism by which mentioned drugs obstructed this pathway is still unclear (Gupta et al 2005). In concordance with previous data, Saq down-regulated Akt phosphorylation in both C6 and B16 cells, which resulted in decreased activity of this kinase. Rate of Akt inhibition correlated with down-regulation of tumor cell viability indicating the relevance of this signalling pathway in tumoricidal activity of the drug. Besides, decreased activity of Akt could be related to Saq capacity to promote differentiation of melanoma cells to melanocytes. It was shown that cAMP elevating agent forskolin induces differentiation of B16 cells by inhibiting this pathway (Busca et al 1996). Oppositely, treatment of B16 with Saq-$NO_2$ induced transient activation of Akt. Similar activation of Akt was observed during differentiation of endothelial cells, osteoblasts and myoblasts (Marchetti et al., 2006, Raucci A et al. 2008, Horowitz JC et al. 2007). Interestingly, neutralization of Akt by specific Akt inhibitor or inhibitor of upstream PI-3K resulted in further decrease of cell viability. The data suggested that conserved anti-tumor properties of $NO_2$-modified compound was not a consequence of its capacity to modulate Akt phosphorilation. This was quite opposite to the attitude that this signal presents one of the major targets through which Saq accomplished its tumoricidal activity. Moreover, Saq-$NO_2$ through temporary but powerful stimulation of Akt delivered protective signal to cell and could be the cause of the lack of drug toxicity against primary cells. The feature of original compound- Saq, to down-regulate PI-3K- Akt pathway dramatically affected the propagation of signal triggered by insulin receptor ligation, disturbing this process and causing the insulin resistance (Gupta et al, 1995). This is the basic event that could be responsible for one of the most serious side effects of the compound. The lack of this destructive signal with conserved antitumor feature, presents a great advantage of newly synthesized drug in comparison to parental compound. Moreover, strong in vivo antimelanoma potential of Saq-$NO_2$ with complete absence of toxicity confirmed in vivo provide a powerful motive for assessment of Saq-$NO_2$ as a promising anticancer drug.

Moreover, Saq-$NO_2$ shows an in-vitro anti-HIV activity on CCR% e CXCR4 strains which is at least as high as that of Saquinavir.

The addition of an $NO_2$ moiety to other protease inhibitor structurally similar to Saquinavir (e.g. Ritonavir, Nelfinavir, Indinavir, Darunavir, Lopinavir, Amprevanir, Atazanavir and the like) imparts favourable properties, similar to that discussed above for Saq-$NO_2$.

Figure Legends

FIG. 1. Synthesis of Saq-$NO_2$.

Figure 2:
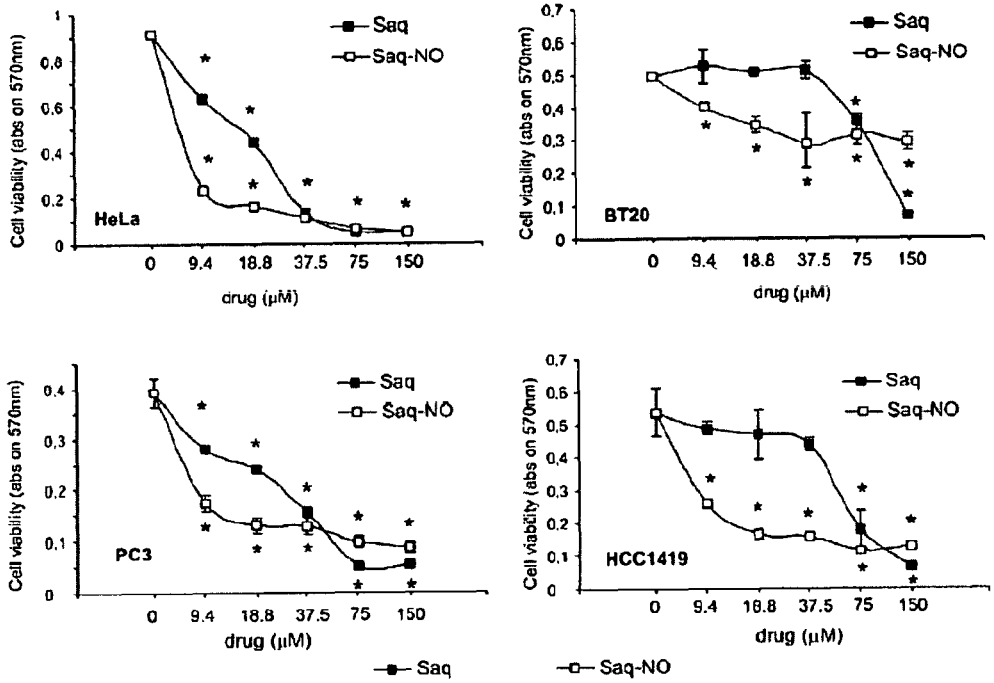
Figure 2:
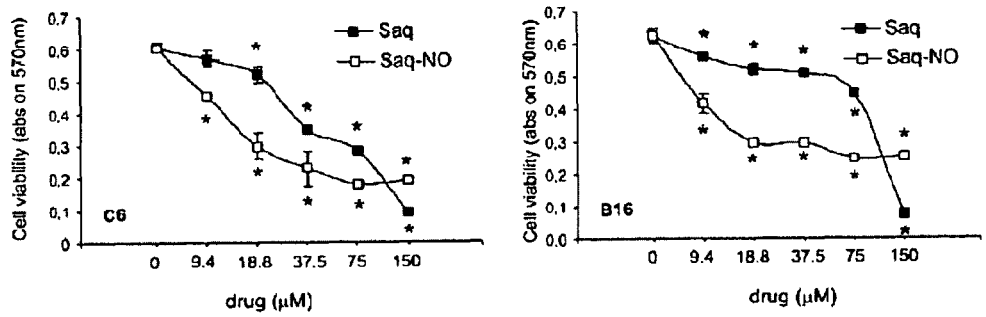
Figure 2:
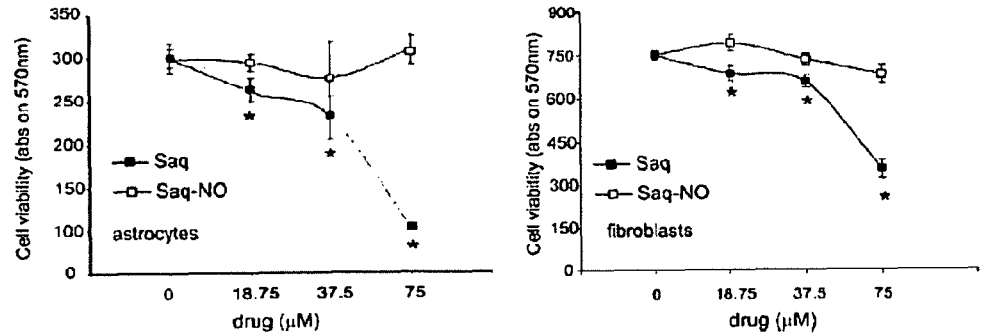

FIG. 2. Cell toxicity of Sag-$NO_2$ versus Sag. Sag-$NO_2$ down-regulates the viability of tumor but not primary cells. Human (A) and rodent (B) tumor cell lines ($1 \times 10^4$ cells/well) and primary/nontransformed rodent cells ($3 \times 10^4$ cells/well) (C) were exposed to varying concentrations of either Sag or saq-$NO_2$ for 24 h. Cell viability was then evaluated by CV test. The data are presented as mean±SD from representative of three independent experiment. *$p<0.05$, refers to untreated cultures.

Figure 3:
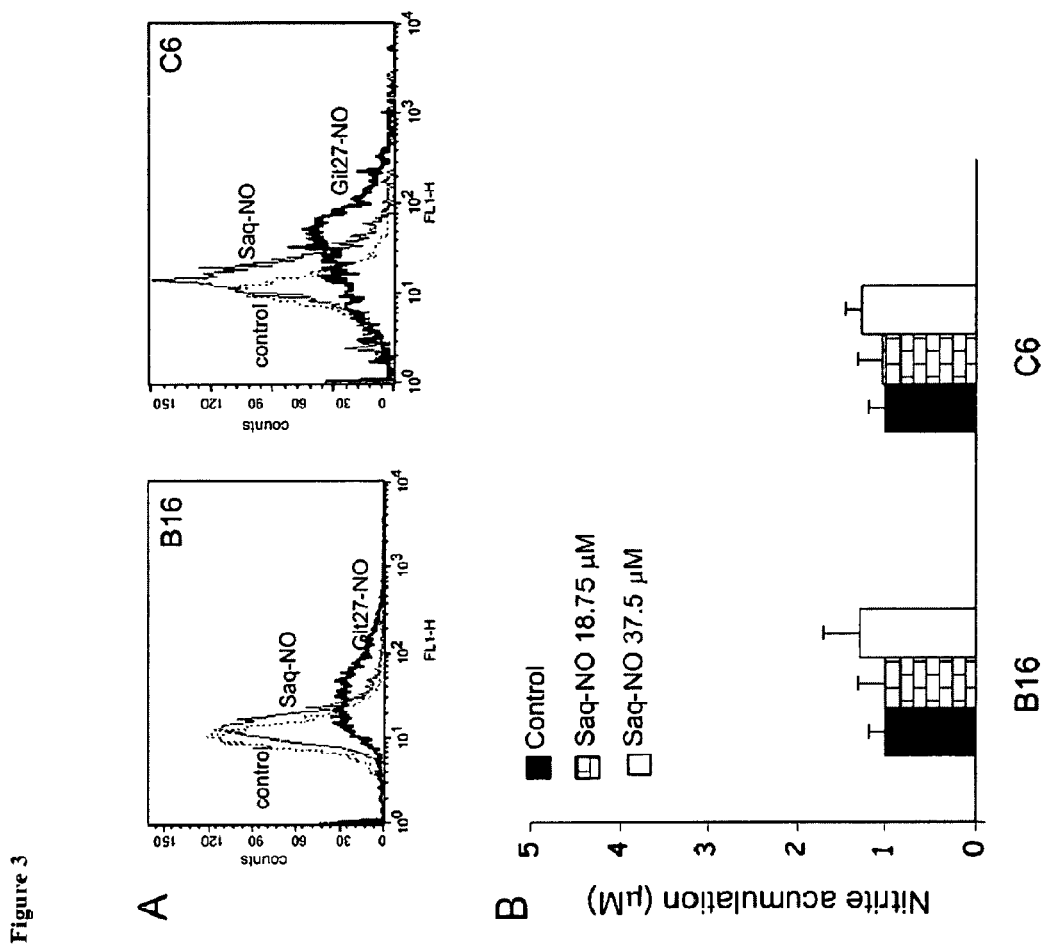

FIG. 3. Tumor cell treatment with Saq-$NO_2$ was followed with negligible $NO_2$ release. (A) Intracellular $NO_2$ was detected by flow cytometry of DAF-FM diacetate stained cells after 24 h of incubation of cells without (control) or with Saq-$NO_2$ (18.8 µM). GIT-27NO (75 µM) treated cells were used as positive control. (B) Accumulation of nitrites in cell culture supernatants was detected after 24 h of incubation of cells with indicated concentrations of Saq-$NO_2$. The data are presented as mean±SD from representative of three independent experiment. *$p<0.05$, refers to untreated cultures.

Figure 4:
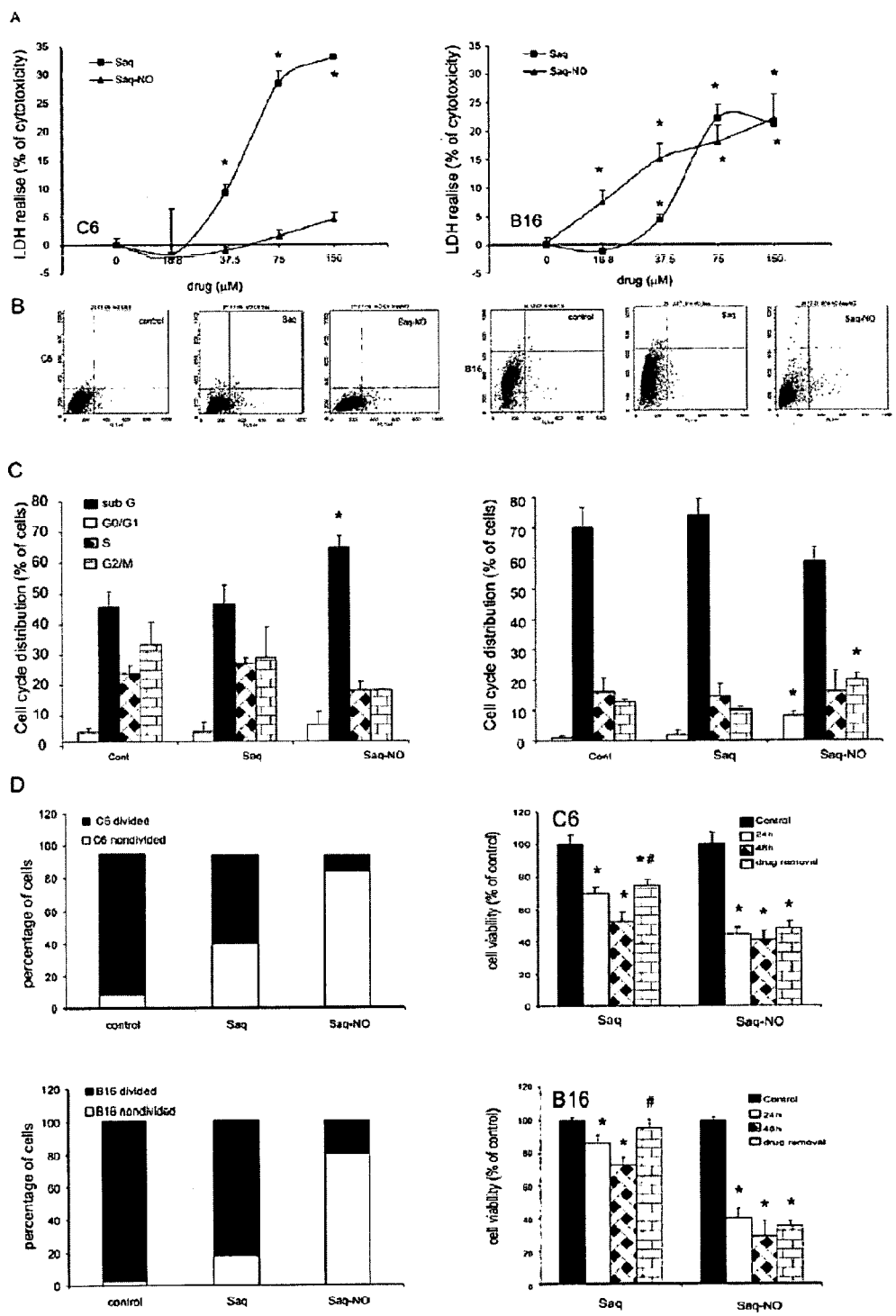

FIG. 4. Saq-$NO_2$ strongly inhibited cell proliferation with minor contribution of cell death. (A) Tumor cells were incubated with different doses of Saq or Saq-$NO_2$ for 24 h, and LDH release assay was performed. Results are calculated as indicated in materials and methods and presented as mean±SD from representative of three independent experiment (*p <0.05). Tumor cells were incubated with 18.8 µM of Saq or Saq-$NO_2$. After 24 h of cultivation without or with drugs, cells were stained with AO orange (B) or PI (C) and analyzed by flow cytometry. The data are presented as mean±SD from three independent experiments. *$p<0.05$, refers to untreated cultures. (D) Cells were stained with CFSE, incubated for 48 h with 18.8 µM Saq or Saq-$NO_2$ and the rate of proliferation was determined by flow cytometry (left panels). Cells were incubated with 18.8 µM of Sag or Saq-$NO_2$ for 24 h. After that, the drugs were either removed or not from the cells and incubated for additional 24 h. Cell viability was determined by CV test after 24 and 48 h of incubation (right panels). The data are presented as mean±SD from three independent experiments. *$p<0.05$, refers to untreated cultures.

Figure 5:
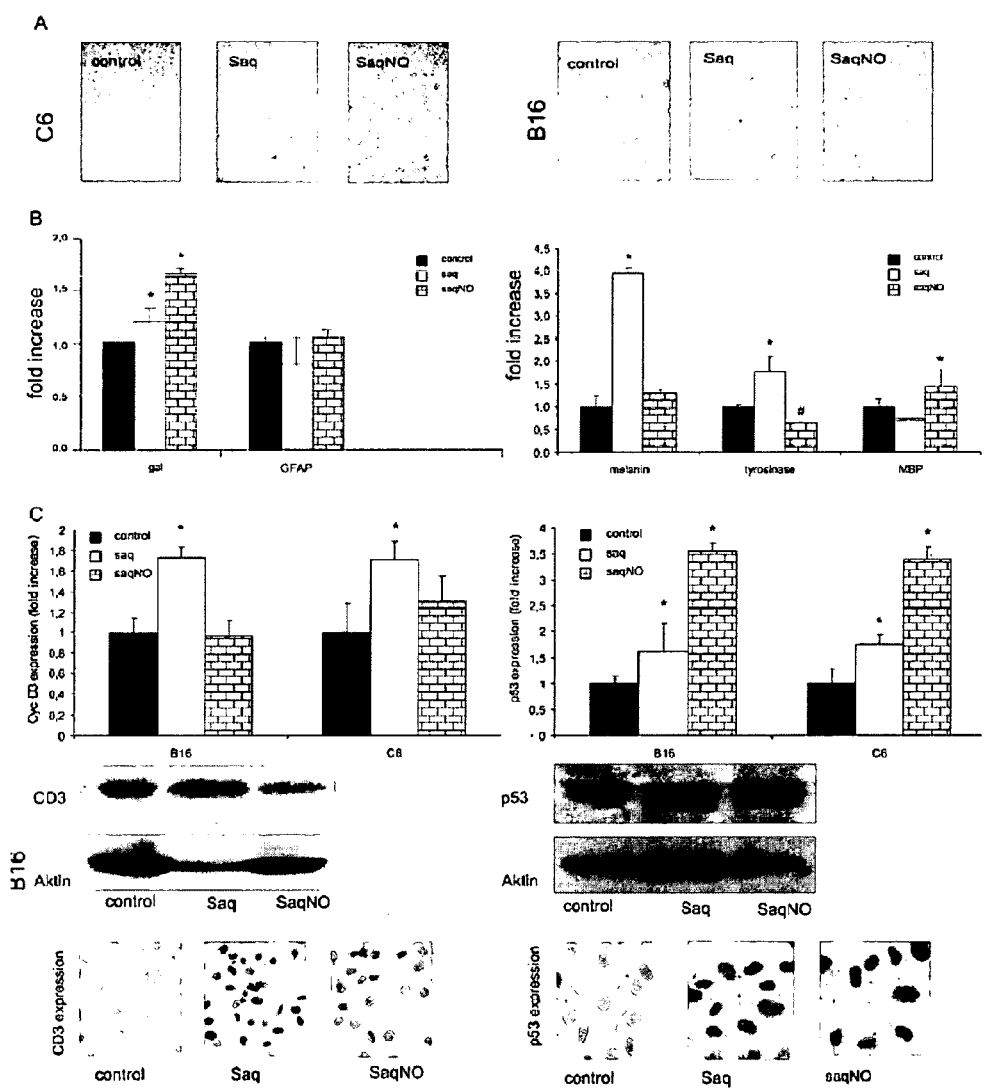

FIG. 5. Saq and Saq-$NO_2$ induce differentiation of C6 and B16 cells. C6 and B16 cells were incubated for 24 h with 18.8 µM Saq or Saq-$NO_2$. Cell morphology was assessed by light microscopy (A). Markers of cell differentiation of C6 and B16 cells, galactocerebroside, GFAP and MBP were determined by cELISA and melanin and tyrosinase activity were determined as described in material and methods (B). Cyclin D3 and p53 expression were evaluated by cELISA (C, upper panels), immunocytochemistry (C, middle panel) and Western blot (C, lower panel). The results were presented as mean±SD from three independent experiments. *$p<0.05$, refers to untreated cultures.

Figure 6:
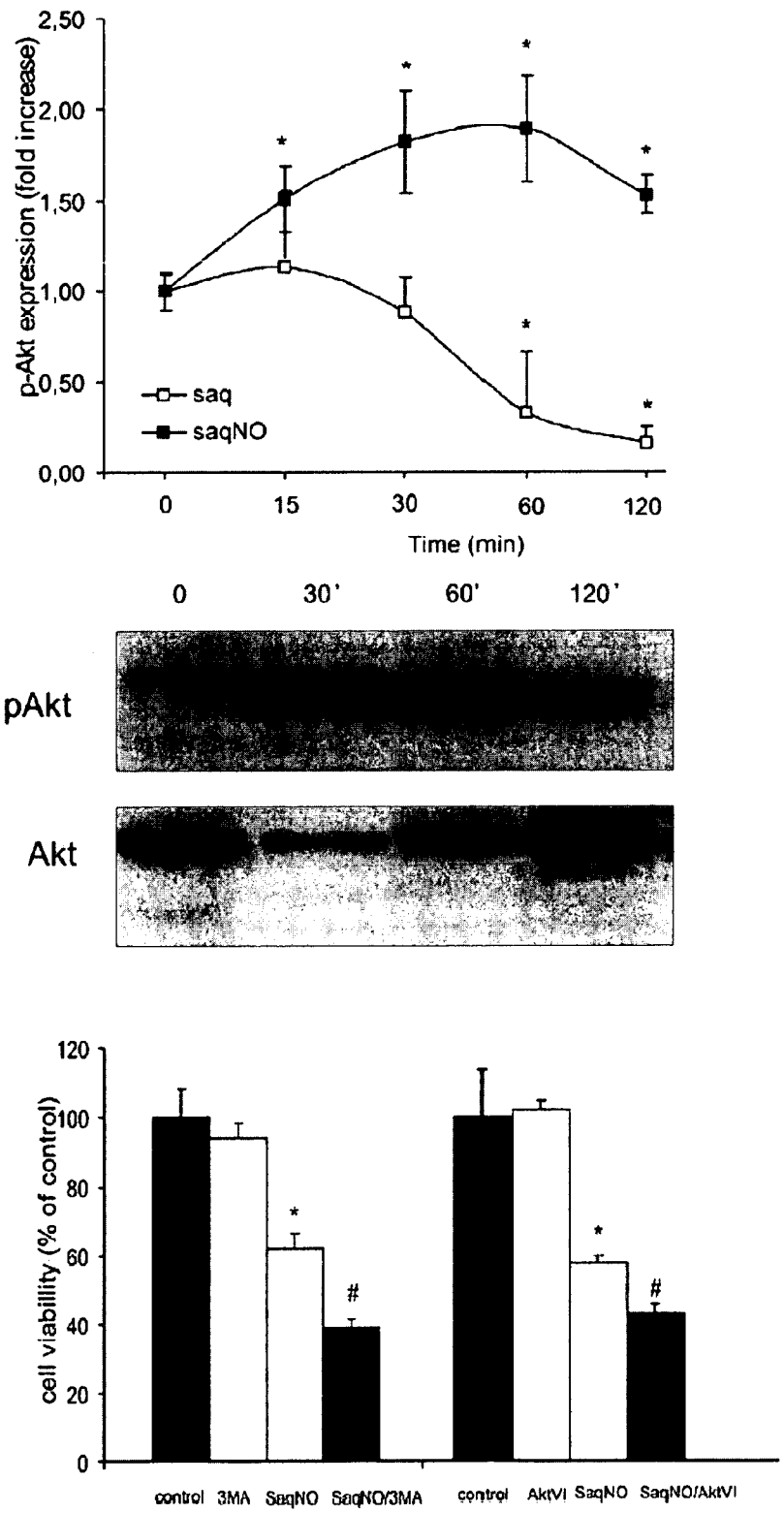

FIG. 6. Saq and Saq-$NO_2$ oppositely regulate Akt activity. (A) B16 cells were incubated with 18.8 µM Saq or Saq-NO and Akt activity was assessed by cELISA and the data are presented as fold increase relative to values obtained in untreated control cultures (*p 0.05). Saq-$NO_2$ effects were confirmed by Western blot (B) at indicated time-points. (C) B16 cells ($1 \times 10^4$ cells/well) were incubated for 24 h with 18.8 µM Saq-$NO_2$ with or without Akt VI (50µg/ml) or 3-MA (1 mM) and cell viability was assessed by MTT. The data are presented as mean±SD from three independent experiments. *$p<0.05$, refers to untreated cultures.

FIG. 7. Saq and Saq-$NO_2$ inhibited the growth of melanoma in C57BL/6 mice. Tumors were induced by s.c. implantation of $2.5 \times 10^5$ B16 melanoma cells and Saq or Saq-$NO_2$ were injected i.p. for 15 consecutive days starting from day 10 after tumor implantation. Tumor volumes were determined 30 days after tumor implantation, as indicated in Materials and methods.

Reference

Mijatovic S, Maksimovic-Ivanic D, Radovic J, Miljkovic Dj, Harhaji Lj, Vuckovic O, Stosic-Grujicic S, Mostarica Stojkovic M, Trajkovic V. (2005) Anti-glioma action of aloe emodin: the role of ERK inhibition. Cell Mol Life Sci 62: 589-98.

Mijatovic S, Maksimovic-Ivanic D, Radovic J, Popadic D, Momcilovic M, Harhaji Lj, Miljkovic D, Trajkovic V. Aloe-emodin prevents cytokine-induced tumor cell death: the inhibition of auto-toxic nitric oxide release as a potential mechanism. (2004) Cell Mol Life Sci 61:1805-15.

Kang W, Nielsen O, Fenger C, Leslie G, Holmskov U, Reid K B. Induction of DMBT1 expression by reduced ERK activity during a gastric mucosa differentiation-like process and its association with human gastric cancer. (2005) Carcinogenesis 26:1129-37.

Decker T, Lohmann-Matthes M L. A quick and simple method for the quantitation of lactate dehydrogenase release in measurements of cellular cytotoxicity and tumor necrosis factor (TNF) activity. (1998) J Immunol Methods 115: 61-9.

Kanzawa T, Germano I M, Komata T, Ito H, Kondo Y, Kondo S. Role of autophagy in temozolomide-induced cytotoxicity for malignant glioma cells. (2004) Cell Death Differ 11:448-57.

Versteeg H H, Nijhuis E, van den Brink G R, Evertzen M, Pynaert G N, et al. A new phosphospecific cell-based ELISA for p42/p44 mitogen-activated protein kinase (MAPK), p38 MAPK, protein kinase B and cAMP-response-element-binding protein. (2000) Biochem J 350: 717-22.

Gupta A K, Cerniglia G J, Mick R, McKenna W G, Muschel R J. HIV protease inhibitors block Akt signalling and radiosensitize tumor cells both in vitro and in vivo. (2005) Cancer Res 65:8256-65.

Ikezoe T, Hisatake Y, Takeuchi T, Ohtsuki Y, Yang Y, Said J W, Taguchi H, Koeffler H P. HIV-1 protease inhibitor, ritonavir: a potent inhibitor of CYP3A4, enhanced the anticancer effects of docetaxel in androgen-independent prostate cancer cells in vitro and in vivo. (2004) Cancer Res 64:7426-31.

Ikezoe T, Saito T, Bandobashi K, Yang Y, Koeffler H P, Taguchi H. HIV-1 protease inhibitor induces growth arrest and apoptosis of human multiple myeloma cells via inactivation of signal transducer and activator of transcription 3 and extracellular signal-regulated kinase ½. (2004) Mol Cancer Ther 3:473-9.

Sgadari C, Monini P, Barillari G, Ensoli B. Use of HIV protease inhibitors to block Kaposi's sarcoma and tumour growth. (2003) Lancet Oncol 4:537-47.

Gills J J, Lopiccolo J, Tsurutani J, Shoemaker R H, Best C J, Abu-Asab M S, Borojerdi J, Warfel N A, Gardner E R, Danish M, Hollander M C, Kawabata S, Tsokos M, Figg W D, Steeg P S, Dennis P A. Nelfinavir, A lead HIV protease inhibitor, is a broad-spectrum, anticancer agent that induces endoplasmic reticulum stress, autophagy, and apoptosis in vitro and in vivo. (2007) Clin Cancer Res 13:5183-94.

Chow W A, Guo S, Valdes-Albini F. Nelfinavir induces liposarcoma apoptosis and cell cycle arrest by upregulating sterol regulatory element binding protein-1. (2006) Anticancer Drugs 17:891-903.

Cuneo K C, Tu T, Geng L, Fu A, Hallahan D E, Willey C D. HIV protease inhibitors enhance the efficacy of irradiation. (2007) Cancer Res 67:4886-93.

Pajonk F, Himmelsbach J, Riess K, Sommer A, McBride WH. The human immunodeficiency virus (HIV)-1 protease inhibitor saquinavir inhibits proteasome function and causes apoptosis and radiosensitization in non-HIV-associated human cancer cells. (2002) Cancer Res 62:5230-5.

Sgadari C, Barillari G, Toschi E, Carlei D, Bacigalupo I, Baccarini S, Palladino C, Leone P, Bugarini R, Malavasi L, Cafaro A, Falchi M, Valdembri D, Rezza G, Bussolino F, Monini P, Ensoli B. HIV protease inhibitors are potent antiangiogenic molecules and promote regression of Kaposi sarcoma. (2002) Nat Med 3:225-32.

Ikezoe T, Daar E S, Hisatake J, Taguchi H, Koeffler H P. HIV-1 protease inhibitors decrease proliferation and induce differentiation of human myelocytic leukemia cells. (2000) Blood 96:3553-9.

Tsai Y J, Chen I L, Horng L Y, Wu R T. Induction of differentiation in rat C6 glioma cells with saikosaponins. Phytother Res (2002) 16: 117-21.

Busca R, Bertolotto C, Ortonne J P, Ballotti R. Inhibition of the phosphatidylinositol 3-kinase/p70(S6)-kinase pathway induces B16 melanoma cell differentiation. (1996) J Biol Chem 271:31824-30.

Busca R, Bertolotto C, Abbe P, Englaro W, Ishizaki T, Narumiya S, Boquet P, Ortonne J P, Ballotti R. Inhibition of Rho is required for cAMP-induced melanoma cell differentiation. (1998) Mol Biol Cell 9:1367-78.

Valverde P, Garcia-Borron J C, Jimenez-Cervantes C, Solano F, Lozano J A. Tyrosinase isoenzymes in mammalian melanocytes. 2. Differential activation by alpha-melanocyte-stimulating hormone. (1993) Eur J Biochem 217:541-8.

Bennett D C, Holmes A, Devlin L, Hart I R. Experimental metastasis and differentiation of murine melanoma cells: actions and interactions of factors affecting different intracellular signalling pathways. (1994) Clin Exp Metastasis 12:385-97.

Ohguchi K, Banno Y, Akao Y, Nozawa Y. Involvement of phospholipase D1 in melanogenesis of mouse B16 melanoma cells. (2004) J Biol Chem 279:3408-12.

Gruber J R, Ohno S, Niles R M. Increased expression of protein kinase C alpha plays a key role in retinoic acid-induced melanoma differentiation. (1992) J Biol Chem 267: 13356-60.

Zhao X, Wakamatsu Y, Shibahara M, Nomura N, Geltinger C, Nakahara T, Murata T, Yokoyama K K. Mannosylerythritol lipid is a potent inducer of apoptosis and differentiation of mouse melanoma cells in culture. (1999) Cancer Res 59:482-6.

Deeks S G, Smith M, Holodniy M, Kahn J O. HIV-1 protease inhibitors. A review for clinicians. (1997) JAMA 277: 145-53.

Maksimovic-Ivanic D, Mijatovic S, Harhaji L, Miljkovic D, Dabideen D, Fan Cheng K, Mangano K, Malaponte G, Al-Abed Y, Libra M, Garotta G, Nicoletti F, Stosic-Grujicic S. Anticancer properties of the novel nitric oxide-donating compound (S,R)-3-phenyl-4,5-dihydro-5-isoxazole acetic acid-nitric oxide in vitro and in vivo. (2008) Mol Cancer Ther 7:510-20.

Nguyen A T, Gagonon A M, Angel J B, Sorisky A. Ritonavir increases the level of active ADD-1/SREBP-1 protein during adipogenesis. (2000) AIDS14:2467-73.

Gruber A, Wheat J C, Kuhen K L, Looney D J, Wong-Staal F. Differential effects of HIV-1 protease inhibitors on dendritic cell immunophenotype and function. (2001) J of Biol Chem 276: 47840-3.

Andre P, Groettrup M, Klenerman P, de Guili R, Booth B L, Cerundolo V, Bonneville M, Jotereau F, Zinkernagel R M, Lotteau V. An inhibitor of HIV-1 protease modulates protease activity, antigen presentation and T cell responses. (1998) Proc Natl Acad Sci 95:13120-4.

Delmonte O M, Bertolotto G, Ricotti E, Tovo P A. Immunomodulatory effect of two HIV protease inhibitors, saquinavir and ritonavir, on lymphocytes from healthy seronegative individuals. (2007) Immunol Letters 111: 111-5.

Flexner C. HIV-protease inhibitors. (2006) Drug therapy 338: 1281-92.

Raucci A, Bellosta P, Grassi R, Basilico C, Mansukhani A Osteoblast proliferation or differentiation is regulated by relative strengths of opposing signalling pathways 2008. J Cell Physiol. 215(2):442-51.

Horowitz J C, Rogers D S, Sharma V, Vittal R, White E S, Cui Z, Thannickal V J.

Combinatorial activation of FAK and AKT by transforming growth factor-beta1 confers an anoikis-resistant phenotype to myofibroblasts. Cell Signal. 2007 April; 19(4):761-71. Epub 2006 Nov. 17.

Slutsky S G, Kamaraju A K, Levy A M, Clebath J, Revel M Activation of myelin genes during transdifferentiation from melanoma to glial cell phenotype (2003). J of Biol Chem 278:8960-8.

Billon N, Terrinoni A, Jolicoeur C, McCarthy A, Richardson W D, Melino G, Raff M. Roles of p53 and p73 during oligodendrocytes development (2003) Development 131:1211-20.

Marchetti V, Menghini R, Rizza S, Vivanti T, Lauro D, Fukamizu A, Lauro R, Federici M Benfotiamine counteracts glucose toxicity effects on endothelial progenitor cell differentiation vs Akt/Fox signalling (2006) Diabetes 55:2231-7.

Kronfeld I, Zsukerman A, Kazimirsky G, Brodie C. Staurosporine induces astrocytic phenotypes and differential expression of specific PKC isoforms in C6 glial cells (1995) J.

J. Neurosci. 1995 September; 15(9):6200-12.

Sasaki T, Yamazaki K, Yamori T, Endo T. Inhibition of proliferation and induction of differentiation of glioma cells with Datura stramonium agglutinin (2002) Br J. Cancer. 87(8):918-23.

Rigas B, Kashfi K. Nitric-oxide-donating NSAIDs as agents for cancer prevention. (2004) Trends Mol Med 10:324-30.

Reed J A, Finnerty B, Albino A P Divergent cellular differentiation pathways during the invasive stage of cutaneous malignant melanoma progression (1999) Am J Pathol 155(2): 549-55.

Yasuhito M. Tokumoto, Be' atrice Durand, 1 and Martin C. Raff (1999) An Analysis of the early events when oligodendrocyte precursor cells are triggered to differentiate by Thyroid Hormone, Retinoic Acid, or PDGF Withdrawal Developmental Biology 213, 327-339.

Bartkova, J., Lukas, J., Strauss, M., and Bartek, J. (1998). Cyclin D3:Requirement for G1/S transition and high abundance in quiescent tissues suggest a dual role in roliferation and differentiation. Oncogene 17, 1027-1037.

Jahn, L., Sadoshima, J.-I., and Izumo, S. (1994). Cyclins and cyclin dependent kinases are differentially regulated during terminal differentiation of C2C12 mouse cells. Exp. Cell Res. 212, 297-307.

Kiess, M., Gill, R. M., and Hamel, P. A. (1995). Expression of the positive regulator of cell cycle progression, cyclin D3, is induced during differentiation of myoblasts into quiescent myotubes. Oncogene 10, 159-166.

Rao, S. S., and Kohtz D. S. (1995). Positive and negative regulation of D-type cyclin expression in skeltal myoblasts by basic fibroblast growth factor and transforming growth factor b. J. Biol. Chem. 270, 4093-4100.

Rao, S. S., and Kohtz D. S. (1995). Positive and negative regulation of D-type cyclin expression in skeletal myoblasts by basic fibroblast growth factor and transforming growth factor b. J. Biol.

Johe, K. K., Hazel, T. G., Muller, T., Dugich-Djordjevic, M. M., and McKay, R. D. (1996). Single factors direct the differentiation of stem cells from fetal and adult central nervous system. Genes Dev. 10, 3129-3140.

Ahlgren, S. C., Wallace, H., Bishop, J., Neophytou, C., and Raff, M. C. (1997). Effect of thyroid hormone on embryonic oligodendrocyte precursor cell development in vivo and in vitro. Mol. Cell. Neurosci. 9, 420-432.

Barres, B. A., Lazar, M. A., and Raff, M. C. (1994). A novel role for thyroid hormone, glucocorticoids and retinoic acid in timing oligodendrocyte development. Development 120, 1097-1108.

Ibarrola, N., Mayer-Pro uschel, M., Rodriguez-Pena, A., and Noble, M. (1996). Evidence for the existence of at least two timing mechanisms that contribute to oligodendrocyte generation in vitro. Dev. Biol. 180, 1-21.

The invention claimed is:

1. Nitric esters of HIV protease inhibitors, wherein the HIV protease inhibitors are selected from Saquinavir, Ritonavir, Nelfinavir, Indinavir, Darunavir, Lopinavir, Amprenavir, Atazanavir and wherein the $NO_2$ moiety is introduced directly on the hydroxyl group of said HIV protease inhibitors without an intermediate organic linker.

2. The nitric ester of Saquinavir according to claim 1 of formula I

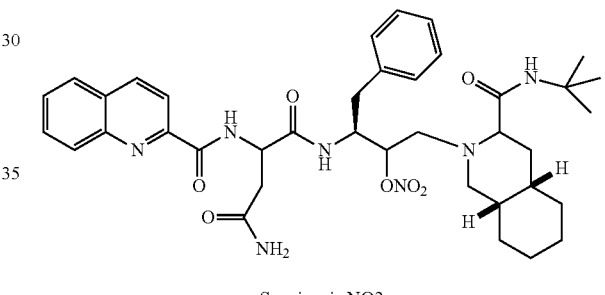

Saquinavir-NO2

3. Pharmaceutical compositions comprising the compounds of claim 1 in admixture with suitable carrier/excipients.

4. A method of treating tumors and/or HIV infections comprising administering to patients in need thereof an effective amount of the compounds of claim 1.

5. A method of treating tumors or HIV infections, said method comprising:
preparing a medicament comprising the compounds of claim 1;
administering an effective amount of said medicament to a patient in need thereof; and:
treating said tumors or said HIV infections.

* * * * *